(12) United States Patent
Font Freide et al.

(10) Patent No.: US 7,034,062 B2
(45) Date of Patent: Apr. 25, 2006

(54) FISCHER-TROPSCH PROCESS

(75) Inventors: Josephus Johannes Helena Maria Font Freide, Guildford (GB); David Newton, Farnham (GB); Christopher Sharp, Beverley (GB)

(73) Assignees: BP Exploration Operatiing Company Limited, London (GB); Davy Process Technology Limited, London (GB)

( * ) Notice: Subject to any disclaimer, the term of this patent is extended or adjusted under 35 U.S.C. 154(b) by 59 days.

(21) Appl. No.: 10/476,245

(22) PCT Filed: May 17, 2002

(86) PCT No.: PCT/GB02/02256

§ 371 (c)(1),
(2), (4) Date: Dec. 17, 2003

(87) PCT Pub. No.: WO02/096833

PCT Pub. Date: Dec. 5, 2002

(65) Prior Publication Data

US 2004/0147621 A1    Jul. 29, 2004

(30) Foreign Application Priority Data

May 25, 2001 (GB) .................................. 0112785
May 25, 2001 (GB) .................................. 0112795
May 25, 2001 (GB) .................................. 0112798

(51) Int. Cl.
*C07C 27/00* (2006.01)

(52) U.S. Cl. ..................... 518/712; 518/711; 518/705; 518/700

(58) Field of Classification Search ................ 518/711, 518/712, 705, 700
See application file for complete search history.

(56) References Cited

U.S. PATENT DOCUMENTS 6,822,007 B1 * 11/2004 Ketley et al. ................ 518/712

FOREIGN PATENT DOCUMENTS

| GB | 728543 | 4/1955 |
| WO | WO 00/34414 | 6/2000 |
| WO | 01/38269 A1 * | 5/2001 |

* cited by examiner

*Primary Examiner*—J. Parsa
(74) *Attorney, Agent, or Firm*—Nixon & Vanderhye

(57) ABSTRACT

Process for the conversion of synthesis gas to higher hydrocarbons. A gaseous stream comprising synthesis gas is contacted at an elevated temperature and pressure with a suspension comprising a particulate Fischer-Tropsch catalyst suspended in a liquid medium, in a reactor system comprising at least one high shear mixing zone and a tubular loop reactor. The suspension and the gaseous stream are passed through the high shear mixing zone(s) wherein the gaseous stream is broken down into gas bubbles and/or irregularly shaped gas voids. Suspension having gas bubbles and/or irregularly shaped gas voids dispersed therein is discharged from the high shear mixing zone(s) into the tubular loop reactor, the discharged suspension is circulated around the tubular loop reactor, and a product suspension stream comprising at least a portion of the circulating suspension is withdrawn from the tubular loop reactor.

41 Claims, 2 Drawing Sheets

FISCHER-TROPSCH PROCESS

This application is the U.S. National Phase of International Application PCT/GB02/02256, filed May 17, 2002, which designated the U.S.

The present invention relates to a process for the conversion of carbon monoxide and hydrogen (synthesis gas) to liquid hydrocarbon products in the presence of a Fischer-Tropsch catalyst.

BACKGROUND OF THE INVENTION

In the Fischer-Tropsch synthesis reaction a gaseous mixture of carbon monoxide and hydrogen is reacted in the presence of a catalyst to give a hydrocarbon mixture having a relatively broad molecular weight distribution. This product is predominantly straight chain, saturated hydrocarbons which typically have a chain length of more than 2 carbon atoms, for example, greater than 2 carbon atoms. The reaction is highly exothermic and therefore heat removal is one of the primary constraints of all Fischer-Tropsch processes. This has directed commercial processes away from fixed bed operation to slurry systems. Such slurry systems employ a suspension of catalyst particles in a liquid medium thereby allowing both the gross temperature control and the local temperature control (in the vicinity of individual catalyst particles) to be significantly improved compared with fixed bed operation.

Fischer-Tropsch processes are known which employ slurry bubble columns in which the catalyst is primarily distributed and suspended in the slurry by the energy imparted from the synthesis gas rising from the gas distribution means at the bottom of the slurry bubble column as described in, for example, U.S. Pat. No. 5,252,613.

The Fischer-Tropsch process may also be operated by passing a stream of the liquid medium through a catalyst bed to support and disperse the catalyst, as described in U.S. Pat. No. 5,776,988. In this approach the catalyst is more uniformly dispersed throughout the liquid medium allowing improvements in the operability and productivity of the process to be obtained.

We have recently found that a Fischer-Tropsch process may be operated by contacting synthesis gas with a suspension of catalyst in a liquid medium in a system comprising at least one high shear mixing zone and a reactor vessel. The suspension is passed through the high shear mixing zone(s) where synthesis gas is mixed with the suspension under conditions of high shear. The shearing forces exerted on the suspension in the high shear mixing zone(s) are sufficiently high that the synthesis gas is broken down into gas bubbles and/or irregularly shaped gas voids. Suspension having gas bubbles and/or irregularly shaped gas voids dispersed therein is discharged from the high shear mixing zone(s) into the reactor vessel where mixing is aided through the action of the gas bubbles and/or the irregularly shaped gas voids on the suspension. The suspension present in the reactor vessel is under such highly turbulent motion that any irregularly shaped gas voids are constantly coalescing and fragmenting on a millisecond time frame, for example, over a period of up to 500 ms. The transient nature of these irregularly shaped gas voids results in improved heat transfer and mass transfer of gas into the liquid phase of the suspension when compared with a conventional slurry bubble column reactor. The reactor vessel may be a tank reactor in which case a suspension recycle stream is withdrawn from the reactor vessel and may be recycled to the high shear mixing zone(s) via an external conduit. Exothermic heat of reaction may be removed from the system by means of a heat exchanger positioned in the external conduit (external heat exchanger) and optionally by a heat exchanger, for example, cooling tubes or coils positioned within the suspension in the reactor vessel (internal heat exchanger). This process is described in WO 0138269 (PCT patent application number GB 0004444) which is herein incorporated by reference. However, there may be a limit on the temperature to which the suspension may be cooled by the external heat exchanger owing to the risk of quenching the reaction and/or deactivating the catalyst. In the absence of an internal heat exchanger, this may necessitate circulating suspension around the external loop conduit at an uneconomic flow rate. The use of an internal heat exchanger may not entirely overcome this problem since there is a risk that an internal heat exchanger may interfere with the process fluid-dynamics, for example, causing coalescence of the gas bubbles and/or the irregularly shaped gas voids thereby reducing mass transfer of gas into the liquid phase of the suspension.

SUMMARY OF THE INVENTION

It has now been found that where a slurry process is operated in a reactor system comprising at least one high shear mixing zone and a tubular loop reactor that the exothermic heat of reaction may be readily removed from the system without any risk of quenching the reaction and/or deactivating the catalyst.

Accordingly, the present invention relates to a process for the conversion of synthesis gas to higher hydrocarbons by contacting a gaseous stream comprising synthesis gas, at an elevated temperature and pressure, with a suspension comprising a particulate Fischer-Tropsch catalyst suspended in a liquid medium, in a reactor system comprising at least one high shear mixing zone and a tubular loop reactor wherein the process comprises:

a) passing the suspension and the gaseous stream through the high shear mixing zone(s) wherein the gaseous stream is broken down into gas bubbles and/or irregularly shaped gas voids;
b) discharging suspension having gas bubbles and/or irregularly shaped gas voids dispersed therein from the high shear mixing zone(s) into the tubular loop reactor;
c) circulating the discharged suspension around the tubular loop reactor; and
d) withdrawing a product suspension stream comprising at least a portion of the circulating suspension from the tubular loop reactor.

For avoidance of doubt, conversion of synthesis gas to higher hydrocarbons may be initiated in the high shear mixing zone(s). However, it is envisaged that the majority of the conversion of the synthesis gas to higher hydrocarbons will take place in the tubular loop reactor.

The tubular loop reactor comprises a tubular conduit. Typically, the tubular conduit may have a length of up to 300 metres, preferably up to 250 metres, for example up to 200 metres. Suitably, the tubular conduit may have a length of at least 50 metres, preferably at least 75 metres, for example, at least 100 metres. Preferably, the tubular conduit has a substantially circular or oval cross-section. Preferably, the tubular conduit has a substantially uniform cross-section along its entire length. Typically, the tubular conduit has a circular cross section with an internal diameter of from 0.5 to 10 meters, preferably 1 to 7.5 metres, for example, 2 to 6 metres.

The tubular loop reactor may comprise a single loop or a plurality of loops, preferably 2 or 3 loops. Suitably, each loop comprises substantially straight sections, preferably 4 straight sections linked via curved sections. The tubular loop reactor may be arranged in a substantially vertical plane. However, an advantage of the process of the present invention is that the suspension and the gaseous stream comprising synthesis gas are well mixed within the tubular loop reactor which mitigates the risk of any settling of the particulate catalyst. Accordingly, the tubular loop reactor may be arranged in a substantially horizontal plane. Where the tubular loop reactor comprises a plurality of loops and the reactor is arranged in a substantially horizontal plane, the loops are preferably, stacked above one another.

In order to avoid excessive coalesence of gas bubbles and/or irregularly shaped gas voids which may lead to slug flow in regions of the tubular loop reactor owing to gas becoming disentrained from the suspension, it is preferred to operate the tubular loop-reactor without a permanent headspace.

Suitably, suspension may be circulated around the tubular loop reactor via at least one mechanical pumping means, for example, a paddle or propeller, positioned in the tubular loop reactor. Preferably, the suspension is passed around the loop via at least two mechanical pumping means, more preferably, 2 to 5, for example, 2 to 3 pumping means. These mechanical pumping means may be spaced apart around the loop or may be located together in a section of the loop conduit. Preferably, the mechanical pumping means are spaced apart. Suitably, the power input of the mechanical pumping means is equivalent to an energy dissipation rate of at least 0.5 kW/m$^3$, preferably 0.5 to 25 kW/m$^3$, more preferably 0.5 to 10 kW/m$^3$, most preferably, 0.5 to 2.5 kW/m$^3$ based on the total volume of slurry in the reactor system. For a plant which is designed to produce 30,000 barrels of liquid higher hydrocarbons per day, at least two mechanical pumping means may be required, each pumping means having a power input of at least 7 MegaWatts.

Preferably, the rate of flow of suspension around the loop is in the range 0.2 to 10 ms$^{-1}$, more preferably 0.2 to 5 ms$^{-1}$, for example 0.5 to 1.5 ms$^{-1}$. The volume of suspension circulated around the loop per hour will depend on the production capacity of a commercial plant, which is typically at least 30,000 barrels of liquid higher hydrocarbons per day. Suitably, the suspension is circulated around the loop at a rate of between 10,000 m$^3$ per hour (45,000 gpm) and 50,000 m$^3$ per hour (225,000 gpm) for a 30,000 barrel/day plant. For larger or smaller scale capacity production plants, the rate at which the suspension is circulated around the loop will be pro rata to the size of the plant.

Suitably, the tubular loop reactor has a shell wall with a heat exchange fluid, preferably water, flowing through the shell side in heat exchange relationship with the suspension circulating around the tubular loop conduit thereby assisting in the removal of at least some of the exothermic heat of reaction. The operation of such a shell wall heat exchanger would be well known to the person skilled in the art.

Preferably, additional cooling is provided by an internal heat exchanger, for example cooling tubes or at least one cooling coil or at least one cooling plate. Preferably, the cooling tubes, coil(s) or plate(s) are arranged in straight sections of conduit which offer the minimum interference with the flow of suspension through the tubular loop reactor. The cooling tubes or coil(s) may be finned so as to provide a greater heat transfer surface area within the tubular loop reactor. Preferably, the tubing of the cooling tubes or coil(s) has an outer diameter of between 1.5 and 15 cm, preferably 3 to 5 cm. Preferably, the cooling plate(s) are concertinaed or corrugated so as to increase the heat transfer area. Preferably, the cooling plate(s) have a breadth of 2 to 10 cm and a depth (distance across the folds of the concertinaed plates or between the peaks and troughs of the corrugated plates) of 10 to 50 cm. Suitably, the cooling tubes, coil(s) or plate(s) are arranged in at least one substantially straight section, preferably, in each straight section of the tubular loop reactor.

Suitably, an array of cooling tubes may be positioned within the tubular loop reactor. Where the array is arranged within a straight section of the tubular loop reactor, it is preferred that the cooling tubes of the array are arranged substantially parallel to one another with the longitudinal axes of the cooling tubes aligned with the longitudinal axis of the straight section of the tubular loop reactor. Preferably, the array comprises at least 5 for example at least 10 cooling tubes arranged substantially parallel to one another. Preferably, the cooling tubes are spaced from each other or from the wall of the tubular loop reactor by at least 20 cm, preferably at least 10 cm.

The cooling coil(s) may be in the form of a helix with the coil(s) wound as if along a cylinder (hereinafter "cylinder defined by the helix). Where the cooling coil(s) is arranged within a straight section of the tubular loop reactor, it is preferred that the longitudinal axis of the cylinder defined by the helix is aligned with the longitudinal axis of the straight section of tubular loop reactor. Suitably, the diameter of the cylinder defined by the helix is at least 10 cm thereby providing a passage for the circulating suspension. Suitably, the cooling coil(s) is positioned at least 10 cm from the walls of the tubular loop reactor. An array comprising a plurality of cooling coils, preferably 2 to 5 cooling coils may be positioned in a straight section of tubular loop reactor. Preferably, the cooling coils of the array are spaced apart by at least 10 cm. Suitably, an array of cooling coils may be positioned within each straight section of tubular loop reactor.

Where the cooling plate(s) is arranged in straight section(s) of the tubular loop reactor, it is preferred that the longitudinal axis of the cooling plate(s) is aligned with the longitudinal axis of the straight section(s). An array comprising a plurality of cooling plates, preferably 2 to 5 cooling plates may be positioned in a straight section of tubular loop reactor. Preferably, the cooling plates of the array are spaced apart from each other and from the walls of the tubular loop reactor by at least 10 cm. Suitably, an array of cooling plates may be positioned within each section of tubular loop reactor.

It is also envisaged that further cooling may be provided by withdrawing a portion of the circulating suspension from the tubular loop conduit and recycling the suspension to the tubular loop conduit after this suspension recycle stream has been cooled in an "external" heat exchanger. Thus, the tubular loop conduit may be provided with a by-pass loop conduit fitted with an external heat exchanger.

Further cooling may be provided by introducing a liquid coolant to the tubular loop reactor and/or the high shear mixing zones and/or any by-pass loop conduit. The liquid coolant may be any liquid which is compatible with a Fischer-Tropsch synthesis reaction. Preferably, the liquid coolant which is to be introduced into the reactor system is at a temperature which is substantially below the temperature of the suspension in the reactor vessel. Preferably, the liquid coolant is at a temperature which is at least 25° C. below, more preferably at least 50° C. below, most preferably at least 100° C. below, for example, at least 150° C. below the temperature of the suspension in the reactor vessel. Suitably, the liquid coolant is cooled (e.g. using refrigeration techniques) before being introduced into the reactor system. Preferably, the liquid coolant is cooled to a temperature below 15° C., more preferably, below 10° C.

Preferably, the liquid coolant is a solvent which is capable of vaporizing under the process conditions (i.e. at an elevated temperature and pressure). Such a liquid coolant is hereinafter referred to as "vaporizable liquid coolant"). Without wishing to be bound by any theory it is believed that the latent heat of vaporization of the vaporizable liquid coolant removes at least some of the exothermic heat of reaction from the reactor system.

Suitably, the vaporizable liquid coolant has a boiling point, at standard pressure, in the range of from 30 to 280° C., preferably from 30 to 100° C. Preferably, the vaporizable liquid coolant is selected from the group consisting of aliphatic hydrocarbons having from 5 to 10 carbon atoms, cyclic hydrocarbons (such as cyclopentane and cyclohexane) alcohols (preferably, alcohols having from 1 to 4 carbon atoms, in particular, methanol and ethanol), ethers (for example, dimethyl ether) tetrahydrofuran, glycols and water. In order to simplify the process, it is preferred that the vaporizable liquid coolant is selected from the group consisting of water (a by-product of the Fischer-Tropsch synthesis reaction) and low boiling liquid hydrocarbons produced in the process of the present invention, such as higher hydrocarbons having from 5 to 10 carbon atoms, in particular, pentanes, hexanes, or hexenes.

The reactor system may comprise a plurality of high shear mixing zones, preferably 2 to 50 high shear mixing zones, more preferably 2 to 25 high shear mixing zones, for example 5 to 15 high shear mixing zones. The high shear mixing zones may be spaced apart around the tubular loop reactor thereby ensuring good mixing of the gaseous stream and suspension within the tubular loop reactor. Preferably, a high shear mixing zone is located every 1 to 100 metres, more preferably, every 2 to 50 metres, most preferably, every 5 to 25 metres, for example, every 7.5 to 15 metres along the length of the tubular loop reactor.

Suitably, the volume of suspension present in the high shear mixing zone(s) is substantially less than the total volume of suspension present in the reactor system, for example, less than 20%, preferably less than 10% of the total volume of suspension present in the reactor system.

The high shear mixing zone(s) may comprise any device suitable for intensive mixing or dispersing of a gaseous stream in a suspension of solids in a liquid medium, for example, a rotor-stator device, an injector-mixing nozzle or a high shear pumping means such as a propeller or paddle having high shear blades.

Where the high shear mixing zone(s) is an injector-mixing nozzle, the nozzle may project through the wall of the tubular loop reactor such that the injector-mixing nozzle(s) discharges the suspension having gas bubbles and/or irregularly shaped gas voids (hereinafter "gas voids") dispersed therein into the tubular loop reactor in which case it will be necessary to withdraw suspension from the tubular loop reactor to provide a suspension feed stream to the injector-mixing nozzle(s) via a by-pass conduit(s). However, it is preferred that the injector-mixing nozzle(s) is located within a section of the tubular loop reactor.

The injector-mixing nozzle(s) can advantageously be executed as a venturi tube (c.f. "Chemical Engineers' Handbook" by J. H. Perry, 3$^{rd}$ edition (1953), p. 1285, FIG. 61), preferably an injector mixer (c.f. "Chemical Engineers' Handbook" by J H Perry, 3$^{rd}$ edition (1953), p 1203, FIG. 2 and "Chemical Engineers' Handbook" by R H Perry and C H Chilton 5$^{th}$ edition (1973) p 6–15, FIGS. 6–31) or most preferably as a liquid-jet ejector (c.f. "Unit Operations" by G G Brown et al, 4$^{th}$ edition (1953), p. 194, FIG. 210).

Alternatively, the injector-mixing nozzle(s) may be executed as a venturi plate located within a conduit having an outlet for discharging suspension into the tubular loop reactor but is preferably located within the tubular loop reactor (i.e. constitutes an internal high shear mixing zone). The venturi plate is positioned within the conduit or tubular loop reactor such that the plate forms a transverse partition in the conduit or tubular loop reactor. Suspension is fed to the venturi plate at a sufficiently high pressure to pass through the apertures in the venturi plate while a gaseous stream comprising synthesis gas is drawn into the conduit or tubular loop reactor through at least one opening in its walls or via at least one pipe which projects through the walls of the conduit or tubular loop reactor. Preferably, there are 2 to 50 such openings or pipes. Preferably, the openings or pipes are located immediately downstream of the venturi plate. By immediately downstream is meant that the openings or pipes are located within 50 cm, preferably within 25 cm, more preferably within 10 cm, for example, within 5 cm of the venturi plate. Suitably, the venturi plate has between 2 to 50 apertures. Preferably, the apertures are circular having diameters in the range of 1 mm to 100 mm. Where a venturi plate is located within a conduit which discharges suspension into the tubular loop reactor, the plate is located at or near the outlet of the conduit, preferably, within 50 cm of the outlet, more preferably within 25 cm of the outlet.

Where the injector mixing nozzle(s) is executed as a venturi nozzle(s) (either a conventional venturi nozzle or as a venturi plate), the pressure drop of the suspension over the venturi nozzle(s) is typically in the range of from 1 to 40 bar, preferably 2 to 15 bar, more preferably 3 to 7 bar, most preferably 3 to 4 bar. Preferably, the ratio of the volume of gas ($Q_g$) to the volume of liquid ($Q_l$) passing through the venturi nozzle(s) is in the range 0.5:1 to 10:1, more preferably 1:1 to 5:1, most preferably 1:1 to 2.5:1, for example, 1:1 to 1.5:1 (where the ratio of the volume of gas ($Q_g$) to the volume of liquid ($Q_l$) is determined at the desired reaction temperature and pressure).

It is also envisaged that the injector-mixing nozzle(s) may be executed as a "gas blast" or "gas assist" nozzle where gas expansion is used to drive the nozzle (c.f. "Atomisation and Sprays" by Arthur H Lefebvre, Hemisphere Publishing Corporation, 1989). Where the injector-mixing nozzle(s) is executed as a "gas blast" or "gas assist" nozzle, the suspension of catalyst is fed to the nozzle at a sufficiently high pressure to allow the suspension to pass through the nozzle while the synthesis gas is fed to the nozzle at a sufficiently high pressure to achieve high shear mixing within the nozzle.

Where the injector mixing nozzle(s) is executed as a gas blast or gas assist nozzle(s), the pressure drop of gas over the nozzle(s) is preferably in the range 3 to 100 bar and the pressure drop of suspension over the nozzle(s) is preferably in the range of from 1 to 40 bar, preferably 4 to 15, most preferably 4 to 7. Preferably, the ratio of the volume of gas ($Q_g$) to the volume of liquid ($Q_l$) passing through the gas blast or gas assist nozzle(s) is in the range 0.5:1 to 50:1, preferably 1:1 to 10:1 (where the ratio of the volume of gas ($Q_g$) to the volume of liquid ($Q_l$) is determined at the desired reaction temperature and pressure).

The high shear mixing zone(s) may also be an internal high shear mixing zone(s) comprising a high shear pumping means such as a paddle or propeller having high shear blades, located in a section of the tubular loop reactor. A gaseous stream comprising synthesis gas is injected into the section of the tubular loop reactor either upstream or downstream of the high shear pumping means, preferably, immediately upstream of the high shear pumping means. By immediately upstream or downstream is meant that the gaseous stream is injected into the section of the tubular loop reactor within 1 metre, preferably within 0.5 metres, more preferably within 0.25 metres of the high shear pumping means. The gaseous stream may be injected into the section of the tubular loop reactor by means of a sparger which may be an open-ended pipe which projects through the wall of the tubular loop reactor. Suitably, the open-ended pipe has an outer diameter of 5 to 15 cm, preferably 7.5 to 10 cm. Suitably, the gas sparger may be a perforated pipe or a plate sparger having orifices of 0.25 to 2 cm in diameter, preferably 0.5 to 1 cm in diameter. However, the sparger should not interfere with the flow of suspension to the high shear pumping means. Without wishing to be bound by any theory, the injected gaseous stream is broken down into gas bubbles and/or irregularly shaped gas voids by the fluid shear imparted to the suspension by the high shear pumping means and the resulting gas bubbles become entrained in the circulating suspension.

It is also envisaged that the injector mixing nozzle(s) may be executed as a high shear pumping means located within a conduit having an outlet for discharging suspension into the tubular loop reactor. The high shear pumping means is preferably a paddle or propeller having high shear blades. Suitably, the high shear pumping means is located close to the outlet of the conduit, for example, within 1 metre of the outlet, preferably within 0.5 metres of the outlet. Synthesis gas is injected into the conduit, for example, via a sparger, located either immediately upstream or immediately downstream of the high shear pumping means, for example, within 1 metres, preferably within 0.5 metres, more preferably 0.05 to 0.2 metres of the high shear pumping means. Preferably, the synthesis gas is injected into the conduit immediately upstream of the high shear pumping means.

Where the tubular loop reactor comprises an internal high shear mixing zone(s), the suspension having gas bubbles and/or irregularly shaped gas voids is discharged from the internal high shear mixing zone(s) into the section(s) of the tubular loop reactor which is immediately downstream thereof.

Suitably, the fluid shear imparted to the suspension in the high shear mixing zone(s) breaks down at least a portion of the gaseous reactant stream into gas bubbles having diameters in the range of from 1 µm to 10 mm, preferably from 30 µm to 3000 µm, more preferably from 30 µm to 300 µm which then become entrained in the suspension.

Without wishing to be bound by any theory, it is believed that any irregularly shaped gas voids are transient in that they are coalescing and fragmenting on a millisecond time scale, for example, over a time frame of up to 500 ms. The gas voids have a wide size distribution with smaller gas voids having an average diameter of 1 to 2 mm and larger gas voids having an average diameter of 10 to 15 mm.

Suitably, the process of the present invention is operated with a gas hourly space velocity (GHSV) in the range 100 to 40000 $h^{-1}$, more preferably 1000 to 30000 $h^{-1}$, most preferably 2000 to 15000, for example 4000 to 10000 $h^{-1}$ at normal temperature and pressure (NTP) based on the feed volume of synthesis gas at NTP.

Preferably, product suspension comprising particulate catalyst suspended in the liquid medium and liquid higher hydrocarbons is withdrawn from the tubular loop conduit and is passed to a gas separation zone. The gas separation zone may be operated at a lower pressure than the pressure in the tubular loop reactor. The pressure in the gas separation zone may be 2 bar less, preferably not more than 5 bar less than the pressure in the tubular loop reactor.

Suitably, the gas separation zone has a headspace into which a gaseous phase comprising unconverted synthesis gas, gaseous higher hydrocarbons, carbon dioxide by-product, inert gases (for example, nitrogen), vaporized low boiling liquid hydrocarbons, vaporized water by-product and any vaporized liquid coolant separates. Preferably, the volume of the headspace is not more than 25%, more preferably not more than 10% of the volume of the external gas separation zone. It is envisaged that a heat exchanger, for example, cooling tubes, coils or plates, may be present below the level of suspension in the gas separation zone in order to assist in the removal of exothermic heat of reaction from the reactor system.

A gaseous recycle stream is withdrawn from the headspace of the gas separation zone and is recycled to the high shear mixing zone(s). The gaseous recycle stream is preferably cooled before being recycled to the high shear mixing zone(s), for example, by passing the gaseous recycle stream through a heat exchanger. The gaseous recycle stream may be cooled to a temperature at which a two phase mixture of gas (synthesis gas, methane by-product, gaseous higher hydrocarbons) and condensed liquid (water by-product, low boiling liquid higher hydrocarbons and any liquid coolant) is formed. The condensed liquid may be separated from the gaseous recycle stream, for example, using a suitable gas-liquid separation means (e.g. a hydrocyclone, demister, gravity separator) and at least a portion of the condensed liquid may be recycled to the tubular loop reactor or the high shear mixing zone(s), for example, with fresh liquid coolant. Preferably, excess water by-product is removed from the separated condensed liquids using a suitable separation means (e.g. a decanter), before recycling the condensed liquids to the tubular loop reactor or high shear mixing zone(s). It is envisaged that the heat exchanger and gas-liquid separation means may be combined within a single unit in order to simplify recycling of the gaseous stream.

Fresh synthesis gas (hereinafter "syngas") may be fed to the gaseous recycle stream, either upstream or downstream of the external exchanger. Where the synthesis gas has not been pre-cooled, the synthesis gas may be fed to the gaseous recycle stream upstream of the heat exchanger. Preferably, the gaseous recycle stream is recycled to the high shear mixing zone(s) via a blower or compressor located downstream of the external heat exchanger.

Preferably, a purge stream is taken from the gaseous recycle stream to prevent the accumulation of gaseous by-products, for example, methane, or of any inert gases, in the system. If desired, any gaseous intermediate products may be separated from the purge stream. Preferably, such gaseous intermediate products are recycled to the tubular loop reactor where they may be converted to higher hydrocarbons.

Alternatively, the purge stream may passed to a power generator where combustion of the unconverted synthesis gas, gaseous hydrocarbons, any vaporized low boiling liquid hydrocarbons and any vaporized liquid coolant is used to generate electricity. At least a portion of said electricity may be used in the operation of the reactor system of the process of the present invention.

The power generator usually comprises one or more prime movers. Suitably, the prime mover may be a gas turbine, a steam turbine or a reciprocating internal combustion engine or a combination thereof. Preferably the prime mover is a gas turbine and is usually driven by steam produced from the heat generated upon combustion of the purge stream.

The electricity generated from the purge stream may be used, for example, to operate the ancillary equipment of the reactor system, for example, compressors, slurry pumps, or heat exchangers.

As discussed below, the synthesis gas used in the process of the present invention is preferably derived from a natural gas stream. It is envisaged that a first portion of a natural gas stream may be used to produce synthesis gas and a second portion of the natural gas stream may be passed to a liquefaction unit to produce liquefied natural gas. Preferably at least a portion of the electricity generated from the purge stream may be used in the operation of the liquefaction unit e.g. to power the refrigeration compressors.

In order to ensure that the particulate catalyst remains suspended in the liquid medium and the liquid higher hydrocarbons, in the gas separation zone, degassed product suspension may be withdrawn from at or near the bottom of the gas separation zone and may be at least in part reintroduced to the gas separation zone (via a by-pass loop conduit) at a position below the level of suspension, preferably, immediately below the level of suspension, in the gas separation zone. The product suspension is passed around the by-pass loop conduit via a mechanical pumping, for example i.e. via a mechanical pumping means, for example a slurry pump means, a slurry pump. A side stream of degassed product suspension may be taken from the by-pass loop conduit downstream of the slurry pump and may be passed to a product separation stage where liquid medium and liquid higher hydrocarbons are separated from the particulate catalyst. An advantage of withdrawing degassed product suspension as a side stream downstream of the slurry pump is that the pump can supply sufficient power to overcome any pressure drops in the product separation stage. Alternatively, degassed product suspension may be withdrawn directly from the gas separation zone.

The product separation stage comprises a suitable liquid-solid separation means. Examples of suitable liquid-solid separation means include hydrocyclones, filters, T-pieces, gravity separators and magnetic separators. Alternatively, the liquid medium and liquid higher hydrocarbons may be separated from the catalyst by distillation. Preferably, there are two or more product withdrawal lines (for two or more product side streams), each line leading to a dedicated solid-liquid separation means. This ensures continuous operation of the process by allowing one or more of the solid-liquid separation means to be taken off-line for cleaning. The catalyst is recycled as a concentrated slurry from the solid-liquid separation means to the tubular loop reactor. Suitably, the concentrated slurry is re-pressurized before being introduced into the tubular loop reactor. The separated liquid (liquid medium, liquid higher hydrocarbons any low boiling hydrocarbon solvent and any water by-product) is passed to a product purification stage. The purification stage may be simplified by using a liquid higher hydrocarbon produced in the process of the present invention as the liquid medium which eliminates the requirement to separate the liquid medium from the liquid higher hydrocarbons. In the purification stage, any water by-product is removed from the liquid higher hydrocarbons.

Preferably, the ratio of hydrogen to carbon monoxide in the synthesis gas produced in the synthesis gas production unit is in the range of from 20:1 to 0.1:1, especially 5:1 to 1:1 by volume, typically 2:1 by volume based on the total amount of hydrogen and carbon monoxide introduced to the system. The synthesis gas may contain additional components such as inerts (for example, nitrogen), carbon dioxide, water and unconverted hydrocarbon feedstock.

The synthesis gas may be prepared using any of the processes known in the art including partial oxidation of hydrocarbons, steam reforming, gas heated reforming, microchannel reforming (as described in, for example, U.S. Pat. No. 6,284,217 which is herein incorporated by reference), plasma reforming, autothermal reforming and any combination thereof. A discussion of a number of these synthesis gas production technologies is provided in "Hydrocarbon Processing" V78, N. 4, 87–90, 92–93 (April 1999) and "Petrole et Techniques", N. 415, 86–93 (July–August 1998). It is also envisaged that the synthesis gas may be obtained by catalytic partial oxidation of hydrocarbons in a microstructured reactor as exemplified in "IMRET 3: Proceedings of the Third International Conference on Microreaction Technology", Editor W Ehrfeld, Springer Verlag, 1999, pages 187–196. Alternatively, the synthesis gas may be obtained by short contact time catalytic partial oxidation of hydrocarbonaceous feedstocks as described in EP 0303438. Preferably, the synthesis gas is obtained via a "Compact Reformer" process as described in "Hydrocarbon Engineering", 2000, 5, (5), 67–69; "Hydrocarbon Processing", 79/9, 34 (September 2000); "Today's Refinery", 15/8, 9 (August 2000); WO 99/02254; and WO 200023689. Preferably, the synthesis gas is derived from natural gas.

Preferably, the higher hydrocarbons produced in the process of the present invention comprise a mixture of hydrocarbons having a chain length of greater than 5 carbon atoms. Suitably, the higher hydrocarbons comprise a mixture of hydrocarbons having chain lengths of from 5 to about 90 carbon atoms. Preferably, a major amount, for example, greater than 60% by weight, of the higher hydrocarbons have chain lengths of from 5 to 30 carbon atoms. Suitably, as discussed above, the liquid medium comprises one or more higher hydrocarbons which are liquid under the process conditions.

The particulate Fischer-Tropsch catalyst which may be employed in the process of the present invention is any catalyst known to be active in Fischer-Tropsch synthesis. For example, Group VIII metals whether supported or unsupported are known Fischer-Tropsch catalysts. Of these iron, cobalt and ruthenium are preferred, particularly iron and cobalt, most particularly cobalt.

A preferred catalyst is supported on a carbon based support, for example, graphite or an inorganic oxide support, preferably a refractory inorganic oxide. Preferred supports include silica, alumina, silica-alumina, the Group IVB oxides, titania (primarily in the rutile form) and most preferably zinc oxide. The supports generally have a surface area of less than about 100 $m^2/g$, suitably less than 50 $m^2/g$, for example, less than 25 $m^2/g$ or about 5 $m^2/g$.

The catalytic metal is present in catalytically active amounts usually about 1–100 wt %, the upper limit being attained in the case of metal based catalysts, preferably 2–40 wt %. Promoters may be added to the catalyst and are well known in the Fischer-Tropsch catalyst art. Promoters can include ruthenium, platinum or palladium (when not the primary catalyst metal), aluminium, rhenium, hafnium, cerium, lanthanum and zirconium, and are usually present in amounts less than the primary catalytic metal (except for ruthenium which may be present in coequal amounts), but the promoter:metal ratio should be at least 1:10. Preferred promoters are rhenium and hafnium.

The particulate Fischer-Tropsch catalyst may have a mean particle size in the range 10 to 500 microns, preferably 10 to 100 microns, for example, in the range 10 to 30 microns.

Preferably, the suspension of catalyst circulating through the tubular loop reactor comprises less than 50% wt of catalyst particles, more preferably 10 to 40% wt of catalyst particles, most preferably 10 to 30% wt of catalyst particles.

It is also envisaged that inert particles may be added to the suspension of the solid particulate Fischer-Tropsch catalyst. Without wishing to be bound by any theory it is believed that these inert particles may improve the dispersion of the solid particulate Fischer-Tropsch catalyst in the liquid medium, absorb at least a portion of the exothermic heat of reaction by acting as a heat sink, enhance the mixing of the suspension and the synthesis gas by reducing the cohesive forces between the catalyst particles, modify the density of the slurry, or control foaming.

Suitably the inert particles are stable in the suspension under the conditions within the reactor system. Preferably, the inert particles may be formed from a material selected from the group consisting of inorganic materials, ceramics, polymers, carbon, metals and alloys. Typical examples of ceramic materials include silica, alumina, zirconia, titania, zinc oxide, and glass. Suitable polymers may be selected from e.g. polyethylene, polypropylene and polystyrene. Suitable metals and alloys include, e.g., aluminium alloys and stainless steel. Preferably the inert particles may be formed from a material used as the support for the Fischer-Tropsch catalyst. Alternatively the inert particles may comprise spent or deactivated catalyst particles in particular spent or deactivated particulate Fischer-Tropsch catalyst.

The inert particles generally have a surface area of less than about 100 m$^2$/g, preferably less than 40 m$^2$/g, more preferably less than 10 m$^2$/g, for example, about 2 m$^2$/g.

Preferably, the inert particles have an average particle size in the range 0.05 microns to 5 millimeters, usually 1 to 1000 microns and especially 5 to 500 microns e.g. 10–200 microns. The particulate Fischer-Tropsch catalyst and the inert particle(s) may have a different average particle size such that the suspension has a bimodal particle size distribution. Alternatively the particulate Fischer-Tropsch catalyst and the inert particle(s) may be of substantially the same average particle size providing the suspension with a unimodal particle size distribution. When more than one type of inert particle is employed, the particulate Fischer-Tropsch catalyst and the differing inert particles may advantageously have different average particle sizes (multimodal particle size distribution).

Preferably, the weight ratio of the solid particulate Fischer-Tropsch catalyst to the inert particles is in the range of 100:1 to 1:100, preferably 20:1 to 1:2, advantageously 10:1 to 1:1 and especially 5:1 to 2:1.

The process of the invention is preferably carried out at a temperature of 180–380° C., more preferably 180–280° C., for example, 190–240° C.

The process of the invention is preferably carried out at a pressure of 5–50 bar, more preferably 15–35 bar, generally 20–30 bar.

The process of the present invention can be operated in batch or continuous mode, the latter being preferred.

In a continuous process product suspension is continuously removed from the system and is continuously passed to the gas separation zone.

Suitably, in a continuous process, the average residence time of the liquid component of the suspension in the tubular loop reactor is in the range of 15 minutes to 30 hours, preferably 0.5 hour to 15 hours. Thus, on average it will take 15 minutes to 30 hours, preferably 0.5 to 15 hours to replace the liquid component of the suspension. Suitably, the gas residence time in the tubular loop reactor (excluding any high shear mixing zone(s)) is in the range 10 to 420 seconds, preferably 20 to 240 seconds.

It is envisaged that a plurality of product suspension streams may be withdrawn from the tubular loop reactor at different positions along the length of the reactor. Thus, a product suspension which is withdrawn at a point remote from the high shear mixing zone(s) may have a different product distribution (a greater proportion of longer chain higher hydrocarbons) than a product suspension withdrawn at a point close to a high shear mixing zone.

BRIEF DESCRIPTION OF THE DRAWINGS

The invention will now be illustrated with the aid of FIGS. 1 and 2.

FIG. 2A illustrates a longitudinal section of a straight section of the tubular loop reactor while

DETAILED DESCRIPTION OF PREFERRED EMBODIMENTS

Figure 1:
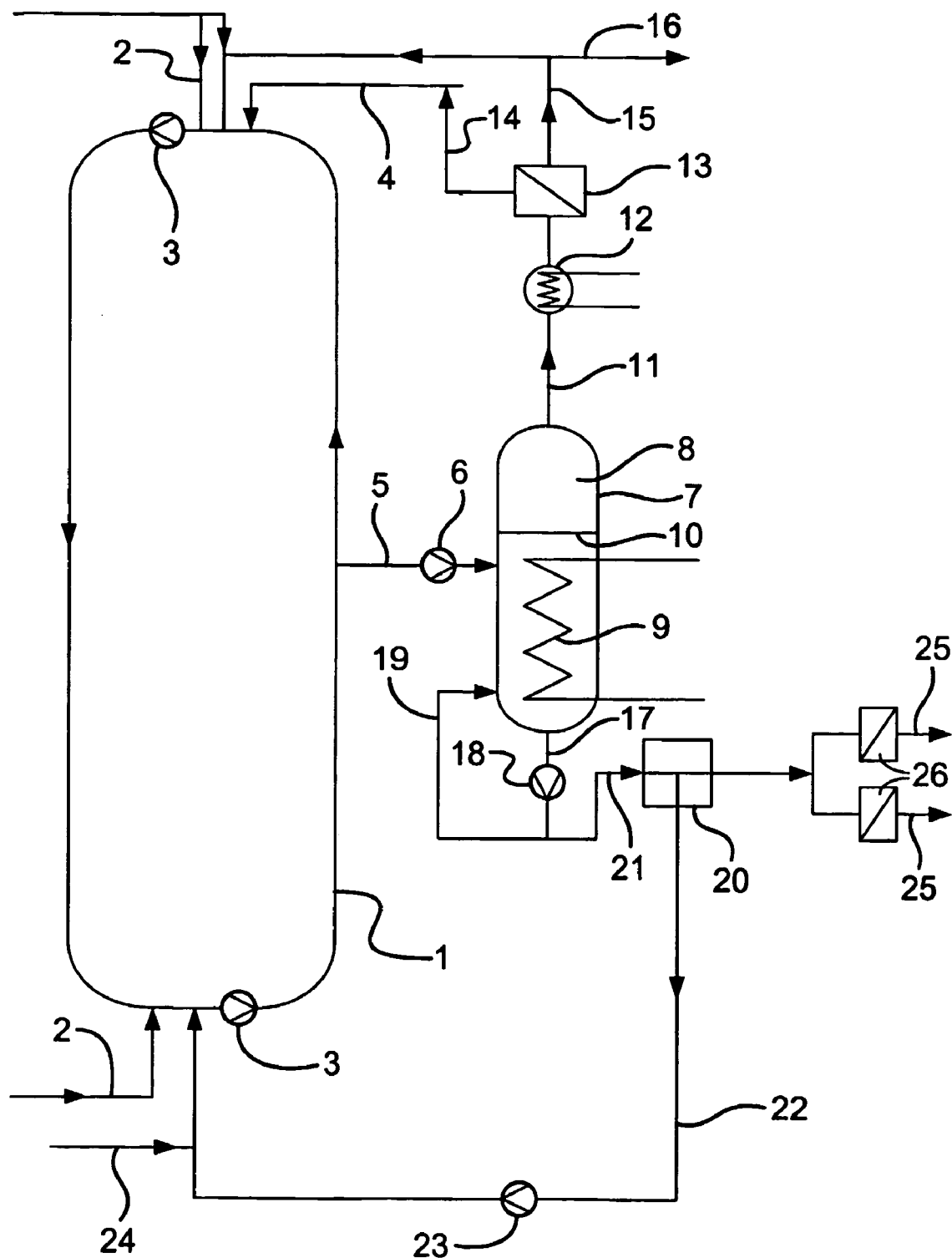
FIG. 1 illustrates a tubular loop reactor system.

In FIG. 1, a tubular loop reactor (1) having a shell wall (not shown) and internal cooling tubes (not shown) is filled with a suspension comprising a particulate Fischer-Tropsch catalyst suspended in a liquid medium. A gaseous reactant stream comprising synthesis gas is introduced to the tubular loop reactor via lines (2) upstream of high shear pumping means (3). The injected gaseous stream is broken down into gas bubbles by the fluid shear imparted to the suspension by the high shear pumping means (3). Thus, the sections of the tubular loop reactor containing the high shear pumping means are internal high shear mixing zones. The high shear pumping means (3) have a further function of circulating the suspension (containing entrained gas bubbles) around the tubular loop reactor (1). Coolant liquid, preferably a vaporizable coolant liquid, may be introduced into the tubular loop reactor upstream of the high shear pumping means via a line (4).

Product suspension is withdrawn from the tubular loop reactor (1) via a line (5) having a slurry pump (6) positioned therein. The product suspension is introduced into a gas separation zone (7). A gas cap (8) is present in the gas separation zone (7) while a heat exchanger (9), for example cooling tubes or coils, is positioned below the level of suspension (10) in the gas separation zone (7).

A gaseous recycle stream typically comprising unconverted synthesis gas, gaseous intermediate products, any vaporized liquid coolant, vaporized low boiling liquid hydrocarbons, and vaporized water by-product may be withdrawn from the gas separation zone (7) through line (11). By means of a heat exchanger (12), the gaseous recycle stream may be cooled to a temperature at which liquid condenses out. The condensed liquid (typically comprising liquid hydrocarbons, water by-product and any coolant liquid) may be separated from the gaseous recycle stream in a gas-liquid separator (13). The condensed liquid may be withdrawn from the gas-liquid separator (13) and may subsequently be recycled to the tubular loop reactor (1), for example, the condensed liquid may be introduced into line (5) via line (14), optionally after having removed at least a portion of the water by-product (not shown). The gaseous recycle stream from the gas-liquid separator (13) is recycled to the tubular loop reactor (1) via line (15). A purge stream may be taken from the gaseous recycle stream via line (16) in order to prevent the build up of gaseous by-products (e.g. methane) in the tubular loop reactor (1).

Degassed and cooled suspension may be withdrawn from the gas separation zone (6) through line (17) and a portion of the withdrawn suspension may be recycled to the gas separation zone (6) via slurry pump (18) and line (19). A portion of the withdrawn suspension is passed to a suitable solid-liquid separator (20) (e.g. a hydrocyclone, a filter, a gravity or magnetic separator, a T-piece separator or a distillation zone) via line (21).

A concentrated catalyst slurry is recycled from the solid liquid separator (20) to the tubular loop reactor (1) via line (22), and slurry pump (23). Fresh gaseous reactant stream or gaseous recycle stream may be mixed with the concentrated catalyst slurry via a line (24).

Hydrocarbon product is removed from the system via lines (25) after fine catalyst particles have been removed in filter/hydrocyclone units (26).

Figure 2A:
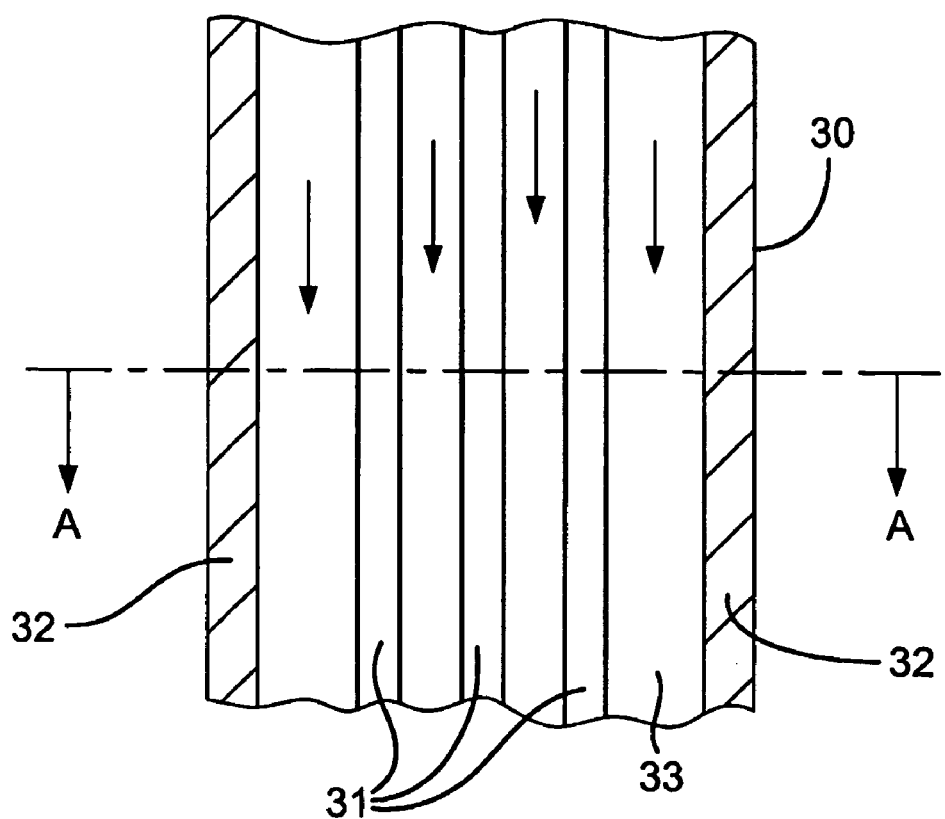

FIG. 2A is a longitudinal section through a straight section of tubular loop conduit (30) having cooling tubes (31) positioned therein. The tubular loop conduit has a shell wall (32). Suspension having gas bubbles dispersed therein (33) is passed through the straight section of tubular loop conduit (30) in the direction indicated by the arrows.

Figure 2B:
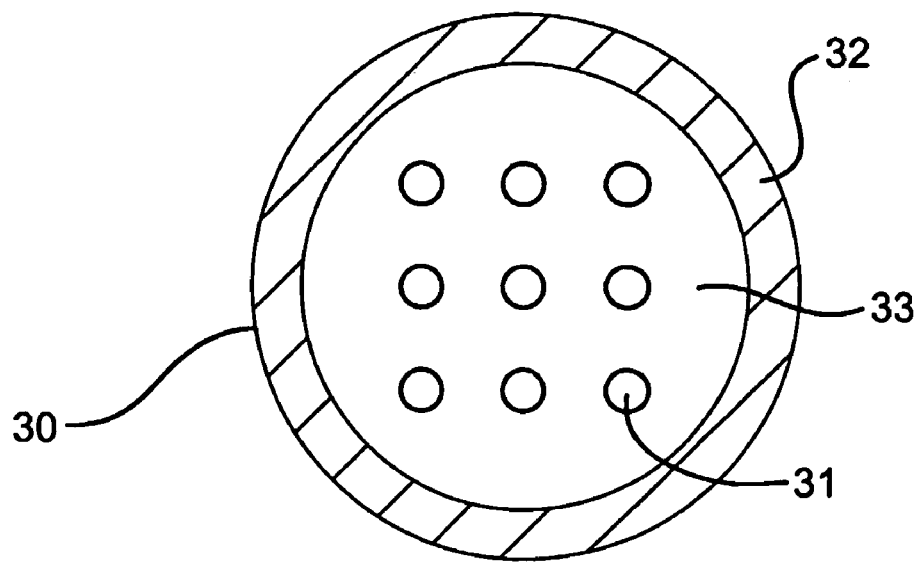
FIG. 2B is a cross section through the straight section of tubular loop reactor taken along AA.

FIG. 2B is a cross-section along AA. The cooling tubes (31) are arranged in rows in a square array.

The invention claimed is:

1. A process for the conversion of synthesis gas to higher hydrocarbons by contacting a gaseous stream comprising synthesis gas, at an elevated temperature and pressure, with a suspension comprising a particulate Fischer-Tropsch catalyst suspended in a liquid medium, in a reactor system comprising at least one high shear mixing zone and a tubular loop reactor wherein the process comprises:
   a) passing the suspension and the gaseous stream through the high shear mixing zone(s) wherein the gaseous stream is broken down into gas bubbles and/or irregularly shaped gas voids;
   b) discharging suspension having gas bubbles and/or irregularly shaped gas voids dispersed therein from the high shear mixing zone(s) into the tubular loop reactor;
   c) circulating the discharged suspension around the tubular loop reactor; and
   d) withdrawing a product suspension stream comprising at least a portion of the circulating suspension from the tubular loop reactor;
   wherein the tubular loop reactor comprises a tubular conduit having a length of 50 to 300 metres.

2. A process as claimed in claim 1 wherein the tubular conduit has a substantially circular cross section with an internal diameter of from 0.5 to 10 metres.

3. A process as claimed in claim 1 wherein the tubular loop reactor comprises 2 or 3 loops with each loop comprising 4 substantially straight sections linked via curved sections.

4. A process as claimed in claim 1 wherein the tubular loop reactor is arranged in a substantially vertical plane or a substantially horizontal plane.

5. A process as claimed in claim 4 wherein the tubular loop reactor comprises a plurality of loops arranged in a substantially horizontal plane with each loop stacked above one another.

6. A process as claimed in claim 1 wherein the tubular loop reactor is operated without a permanent headspace.

7. A process as claimed in claim 1 wherein the suspension is circulated around the tubular loop reactor via 2 to 5 pumping means.

8. A process as claimed in claim 1 wherein the pumping means are spaced apart around the loop reactor.

9. A process as claimed in claim 7 wherein the power input of the pumping means is equivalent to an energy dissipation rate of 0.5 to 10 kW/m$^3$ based on the total volume of slurry in the reactor system.

10. A process as claimed in claim 1 wherein the rate of flow of suspension around the tubular loop reactor is in the range 0.2 to 10 Ms$^{-1}$.

11. A process as claimed in claim 1 wherein the gas hourly space velocity (GHSV) is in the range 2000 to 15000 h$^{-1}$ at normal temperature and pressure (NTP) based on the feed volume of synthesis gas at NTP.

12. A process as claimed in claim 1 wherein the tubular loop reactor has a shell wall with a heat exchange fluid, flowing through the shell side in heat exchange relationship with the suspension circulating around the tubular loop reactor.

13. A process as claimed in claim 1 wherein the tubular loop reactor is provided with at least one internal heat exchanger.

14. A process as claimed in claim 13 wherein the internal heat exchanger(s) comprises at least one array of cooling tubes, cooling coils or cooling plates.

15. A process as claimed in claim 14 wherein the cooling tubes, coils or plates of the array(s) are arranged in straight sections of the tubular loop conduit.

16. A process as claimed in claim 14 wherein the cooling tubes or coils of the array(s) are finned.

17. A process as claimed in claims 14 wherein the tubing of the cooling tubes or coils of the array(s) has an outer diameter of between 1.5 and 15 cm.

18. A process as claimed in claim 14 wherein the cooling tubes of the array(s) are arranged substantially parallel to one another and the longitudinal axes of the cooling tubes are aligned with the longitudinal axis of the straight section (s) of the tubular loop reactor.

19. A process as claimed in claim 18 wherein the array(s) comprise at least 10 cooling tubes and are spaced from each other or from the wall of the tubular loop reactor by at least 20 cm.

20. A process as claimed in claim 14 wherein the cooling coils of the array(s) are in the form of a helix with the coils wound as if along a cylinder and the cooling coils are arranged within a straight section(s) of the tubular loop reactor with the longitudinal axis of the cylinder defined by the helix aligned with the longitudinal axis of the straight section(s) of the tubular loop reactor.

21. A process as claimed in claim 20 wherein the diameter of the cylinder defined by the helix is at least 10 cm and the cooling coils are spaced apart from one another and from the walls of the tubular loop reactor by at least 10 cm.

22. A process as claimed in claim 14 wherein the cooling plate(s) are concertinaed or corrugated and have a breadth of 2 to 10 cm and a depth (distance across the folds of the concertinaed plates or between the peaks and troughs of the corrugated plates) of 10 to 50 cm.

23. A process as claimed in claim 22 wherein the longitudinal axes of the cooling plates are aligned with the longitudinal axis of the straight section(s) of tubular loop reactor.

24. A process as claimed in claim 22 wherein the array comprises 2 to 5 cooling plates which are spaced apart from each other and from the walls of the tubular loop reactor by at least 10 cm.

25. A process as claimed in claim 1 wherein a portion of the circulating suspension is withdrawn from the tubular loop conduit and is at least in part recycled to the tubular loop conduit after having been cooled in an external heat exchanger.

26. A process as claimed in claim 1 wherein a vaporizable liquid solvent is introduced into the tubular loop reactor and/or the high shear mixing zones.

27. A process as claimed in claim 1 wherein the volume of suspension present in the high shear mixing zone(s) is less than 10% of the total volume of suspension present in the reactor system.

28. A process as claimed in claim 1 wherein the reactor system comprises 2 to 50 high shear mixing zones which discharge into or a located within the tubular loop reactor.

29. A process as claimed in claim 28 wherein a high shear mixing zone is located every 2 to 50 metres along the length of the tubular loop reactor.

30. A process as claimed in claim 1 wherein the high shear mixing zone(s) comprises an injector-mixing nozzle.

31. A process as claimed in claim 30 wherein the injector-mixing nozzle(s) is executed as a venturi nozzle or as a gas blast nozzle.

32. A process as claimed in claim 31 wherein the venturi nozzle(s) comprises a venturi plate(s) having apertures therein, the venturi plate(s) being arranged within the tubular loop reactor such that the suspension passes under pressure through the apertures in the venturi plate(s) while a gaseous stream comprising synthesis gas is drawn into the tubular loop reactor downstream of the venturi plate(s) through at least one opening in the walls or the tubular loop reactor through at least one pipe which projects through the walls of the tubular loop reactor.

33. A process as claimed in claim 32 wherein the pressure drop of the suspension over the venturi nozzle(s) is in the range of from 2 to 15 bar and wherein the ratio of the volume of gas ($Q_g$) to the volume of liquid ($Q_l$) passing through the venturi nozzle(s) is in the range 0.5:1 to 10:1 (where the ratio of the volume of gas ($Q_g$) to the volume of liquid ($Q_l$) is determined at the desired reaction temperature and pressure).

34. A process as claimed in claim 31 wherein the high shear mixing zone(s) is executed as a gas blast nozzle(s) having a pressure drop of gas over the nozzle(s) in the range 3 to 100 bar and a pressure drop of suspension over the nozzle(s) in the range of from 4 to 15 bar and wherein the ratio of the volume of gas ($Q_g$) to the volume of liquid ($Q_l$) passing through the gas blast nozzle(s) is in the range 0.5:1 to 50:1(where the ratio of the volume of gas ($Q_g$) to the volume of liquid ($Q_l$) is determined at the desired reaction temperature and pressure).

35. A process as claimed in claim 1 wherein the high shear mixing zone(s) comprising a section of the tubular loop reactor having a high shear pumping means located therein and a gaseous stream comprising synthesis gas is injected into the section of the tubular loop reactor immediately upstream of the high shear pumping means.

36. A process as claimed in claim 35 wherein the synthesis gas is injected into the section of the tubular loop reactor within 1 metre of the high shear pumping means.

37. A process as claimed in claim 1 wherein the fluid shear imparted to the suspension in the high shear mixing zone(s) breaks down at least a portion of the gaseous reactant stream into gas bubbles having diameters in the range of from 1 µm to 10 mm.

38. A process as claimed in claim 1 wherein irregularly shaped gas voids are present in the suspension in the tubular loop reactor and the gas voids are coalescing and fragmenting over a time frame of up to 500 ms.

39. A process as claimed in claim 1 wherein product suspension comprising the particulate Fischer-Tropsch catalyst suspended in the liquid medium and liquid higher hydrocarbons is withdrawn from the tubular loop conduit and is passed to a gas separation zone wherein a gaseous phase is separated from the product suspension and the separated gaseous phase is at least in part recycled to the high shear mixing zone(s).

40. A process as claimed in claim 1 wherein the average residence time of the liquid component of the suspension in the tubular loop reactor is in the range of 15 minutes to 30 hours.

41. A process as claimed in claim 35 wherein the fluid shear imparted to the suspension in the high shear mixing zone(s) breaks down at least a portion of the gaseous reactant stream into gas bubbles having diameters in the range of from 30 µm to 300 µm which then become entrained in the suspension.

* * * * *